United States Patent
Koehler et al.

(10) Patent No.: US 7,778,383 B2
(45) Date of Patent: Aug. 17, 2010

(54) EFFECTIVE DUAL-ENERGY X-RAY ATTENUATION MEASUREMENT

(75) Inventors: Thomas Koehler, Norderstedt (DE); Jens-Peter Schlomka, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 207 days.

(21) Appl. No.: 12/293,564

(22) PCT Filed: Mar. 14, 2007

(86) PCT No.: PCT/IB2007/050879
§ 371 (c)(1), (2), (4) Date: Sep. 19, 2008

(87) PCT Pub. No.: WO2007/110795
PCT Pub. Date: Oct. 4, 2007

(65) Prior Publication Data
US 2010/0166139 A1    Jul. 1, 2010

(30) Foreign Application Priority Data
Mar. 29, 2006   (EP)   ................................. 06111882

(51) Int. Cl.
*A61B 6/00*   (2006.01)
(52) U.S. Cl. ............................ 378/5; 378/19; 378/901
(58) Field of Classification Search ............. 378/4–20, 378/98.11, 98.12, 901
See application file for complete search history.

(56) References Cited

U.S. PATENT DOCUMENTS
5,812,629 A    9/1998   Clauser

FOREIGN PATENT DOCUMENTS
| DE | 3426934 A1 | 5/1985 |
| EP | 0231037 A1 | 8/1987 |
| EP | 0365084 A1 | 4/1990 |

*Primary Examiner*—Courtney Thomas

(57) ABSTRACT

It is described a method and a CT system for measuring dual-energy X-ray attenuation data of an object. The CT system comprises a rotatable holder, an X-ray source comprising two different X-ray focus points, and an X-ray detection device comprising a plurality of detector elements exhibiting different spectral sensitivities. The method comprises the steps of (a) adjusting the X-ray source such that it emits X-rays originating a first focus point, (b) acquiring first attenuation data separately with first detector elements and with second detector elements, (c) moving the X-ray focus discretely to a second focus point, and (d) acquiring second attenuation data separately with both types of detector elements. Thereby the two focus points are spatially separated from each such that a first beam path originating from the first focus point penetrates a certain voxel within the object and impinges on a first detector element and a second beam path originating from the second X-ray focus point penetrates the same voxel and impinges on a second detector element.

18 Claims, 3 Drawing Sheets

EFFECTIVE DUAL-ENERGY X-RAY ATTENUATION MEASUREMENT

The present invention relates to the field of dual-energy X-ray imaging. Thereby, two different images of one and the same object of interest are obtained, whereby for each image x-rays having different X-ray photon energies or a different distribution of photon energies are used. In particular, the present invention relates to a simple and effective method for measuring dual-energy X-ray attenuation data of an object under examination by means of a computed tomography system.

The present invention further relates to a computed tomography system for measuring dual-energy X-ray attenuation data of an object under examination.

Further, the present invention relates to a data processing device for measuring dual-energy X-ray attenuation data by means of a computed tomography system.

Furthermore, the present invention relates to a computer-readable medium and to a program element having instructions for executing the above-mentioned method for measuring dual-energy X-ray attenuation data of an object under examination by means of a computed tomography system.

Dual-energy computed tomography (CT) is a well-known technique, wherein the spectral dependence of the X-ray absorption of an object is measured using two different spectral weighting functions. Preferably, the two spectral weighting functions have none or only a small overlap. Typically, the different spectral attenuation behavior of an object under examination is caused by different physical effects like Photo-effect and Compton scattering. Different materials have a different spectral dependence of the attenuation. Thus, dual-energy CT enables an improved characterization of material.

Dual-energy CT is traditionally implemented by either switching the electron acceleration voltage of an X-ray tube or by using detectors, which a capable to discriminate between two different photon energies. However, tube voltage switching is difficult to achieve in particular within short data acquisition times like typically 300 μs, which is currently state of the art for modern CT systems. On the other hand, detectors comprising an energy resolution are comparatively costly. However, an energy resolution is necessary in order to provide for an energy discrimination of the detected X-ray photons.

EP 0 231 037 A1 discloses an X-ray scanner comprising an array of detector elements and an X-ray tube with elongated anode or double focus. The X-ray scanner can be operated in different modes: (a) The unpaired mode by using all the detector signals separately, (b) the paired mode by combining the signals of two adjacent detector elements, respectively, and (c) the dual-energy mode by selectively attributing different spectral filters to alternating detector elements.

There may be a need for a method and a system for effectively measuring dual-energy X-ray attenuation data of an object under examination.

This need may be met by the subject matter according to the independent claims. Advantageous embodiments of the present invention are described by the dependent claims.

According to a first aspect of the invention there is provided a method for measuring dual-energy X-ray attenuation data of an object under examination by means of a computed tomography system.

Thereby, there is used a computed tomography system comprising a rotatable holder being rotatable around a rotation axis, an X-ray source comprising a first X-ray focus point and a second X-ray focus point, the X-ray source being mounted at the rotatable holder, and an X-ray detection device comprising a plurality of detector elements. The detector elements are divided into a first group of first detector elements and a second group of second detector elements, wherein the first and the second detector elements exhibit different spectral sensitivities, and the X-ray detection device is mounted at the rotatable holder opposite to the X-ray source with respect to the rotation axis.

The described method comprises the steps of (a) adjusting the X-ray source such that it emits X-rays originating from the first X-ray focus point, (b) acquiring first X-ray attenuation data separately with the first detector elements and with the second detector elements, (c) moving the X-ray focus from the first X-ray focus point to the second X-ray focus point, and (d) acquiring second X-ray attenuation data separately with the first detector elements and with the second detector elements. Thereby, the two X-ray focus points are spatially separated from each other such that a first beam path originating from the first X-ray focus point penetrates a certain voxel within the object and impinges on a first detector element and a second beam path originating from the second X-ray focus point penetrates the same voxel and impinges on a second detector element, and wherein the X-ray focus is moved in a discrete manner from the first X-ray focus point to the second X-ray focus point.

This aspect of the invention is based on the idea that if the focus point of the X-ray source jumps by the full radial sampling distance of the physical detector, dual-energy attenuation image data may by acquired in a simple and effective way. Thereby, for each X-ray energy two projection data sets are acquired, which both are sampled with a relatively low spatial resolution. However, it is possible to combine these two projection data sets in order to obtain an X-ray image having improved resolution. This improved resolution corresponds to a resolution, which is achievable with a single X-ray focus point and with one type of detector elements only.

Of course, this combination of two projection data sets may be carried out for both X-ray photon energies such that in the end two different images representing the attenuation of the object at different photon energies may be obtained, wherein each image exhibits the described original resolution. The X-ray beams originating from the two focal points may each have a fan beam geometry or a cone beam geometry. In case of a cone beam geometry a two dimensional detector array may be used in order to exploit all X-ray photons penetrating the object under examination.

According to an embodiment of the present invention, the method further comprises the steps of combining the first X-ray attenuation data acquired with the first detector elements with the second X-ray attenuation data acquired with the first detector elements, and/or combining the first X-ray attenuation data acquired with the second detector elements with the second X-ray attenuation data acquired with the second detector elements.

This has the advantage that the spatial resolution may be improved significantly by a factor of two. As has already been mentioned above, such an enhanced resolution corresponds to a spatial resolution, which would be given if (a) an X-ray source with only one X-ray focus point and (b) a detector with only one type of detector elements is used. After the two different data sets each representing an X-ray attenuation at a certain X-ray photon energy have been obtained, the data analysis may be carried out by applying known standard methods for dual-energy CT image reconstruction.

According to a further embodiment of the invention, the first detector element is impinged by the first beam path and the second detector element is impinged by the second beam path are neighboring detector elements. This has the advantage that there are generated relatively small artifacts only. This is the case because with the same photon energy and at a defined viewing angle (i.e. one angular position of the rotatable holder) neighboring voxels are measured only under slightly different beam path angles.

In this respect it has to be pointed out that the size of the voxels is defined by the spatial resolution of the CT scanner, which depends in particular on the size of the detector elements.

According to a further embodiment of the invention, the steps of adjusting the X-ray source, acquiring first X-ray attenuation data, moving the X-ray focus and acquiring second X-ray attenuation data are carried out at a plurality of different viewing angles defined by the angular position of the rotatable holder. This has the advantage that the attenuation of all voxels within an examination volume may be determined for two different photon energies. If the attenuation at the two different photon energies is predominately based on two different physical attenuation effects being predominately independent from each other (e.g. Photo effect and Compton effect), the X-ray attenuation of these voxels may be computed for a wide range of photon energies.

In case of a fan-beam geometry the examination volume is a slice orientated perpendicular to the rotation axis. However, by shifting the object under examination along the rotation axis and/or by moving the X-ray source and the detection device along a spiral path around the object under study the effective examination volume may be a three-dimensional portion of the object under study.

It has to be pointed out that by using a cone beam geometry the data acquisition may be speeded up in case a two-dimensional detector is employed. According to a further embodiment of the invention, there is generated an attenuation map representing the X-ray attenuation data of a plurality of voxels within the object under examination. The attenuation map is taken into account for a data evaluation of a further medical examination method.

Such a medical examination method may be for instance Positron Emission Tomography (PET) or Single Photon Emission Computed Tomography (SPECT). Thereby, as has already described above, the attenuation map may include the X-ray attenuation for the photon energy, which is used for the further medical examination method. In case of PET, the corresponding photon energy is 511 keV. In case of SPECT, the corresponding photon energy is typically also a monochromatic energy depending on the employed radioactive element.

The data evaluation of a further medical examination method may benefit from a dual-energy attenuation map in the following way: Typically, a dual-energy CT measures two spectral different X-ray attenuations within the diagnostically relevant energy range approximately from 60 keV to 140 keV. Since the photon energy of the further medical examination method is well known (511 keV for PET), one can use the two spectral different energy attenuations for an extrapolation in order to estimate the actual attenuation of the object under examination at the photon energy of the further medical examination method more precisely.

The generation of a preferably three-dimensional attenuation map may provide the advantage that attenuation corrections for the X-ray photons related to the further radiological examination method may be accomplished allowing for a much more precise data evaluation of the data acquired by the further radiological examination method.

It has to be noted that for medical applications, it is often not acceptable to perform a so-called post-patient energy filtering. Thereby, the energy discrimination is carried out by means of X-ray absorbing elements, which are arranged in selected beam paths between the patient and the detector elements. It is clear that such a post-patient energy filtering causes an increased radiation dose, which is usually harmful to the health of the patient. However, the described method for measuring dual-energy X-ray attenuation data by means of a post-patient energy filtering may be acceptable in combination with such further radiological examination methods because in the case of PET and/or SPECT the resulting emission image may benefit significantly from the acquired attenuation map. This holds in particular if the attenuation map is generated by X-ray measurements at a relatively low radiation dose.

According to a further embodiment of the invention, dual-energy X-ray attenuation data of a baggage item are measured. This has the advantage that an effective method is provided allowing for e.g. an identification of explosive materials within baggage items.

At this point it has to be mentioned that apart from baggage items and apart from human or animal beings there are also other types of objects, which may be measured by means of the above-described method. In particular, when measuring non-alive objects, dose issues are typically of secondary importance such that the described method may be carried out with a high photon flux leading to a high accuracy in the measured attenuation data. Further applications for the described method are e.g. three-dimensional material inspections based on dual-energy attenuation measurements.

According to a further embodiment of the invention, the used X-ray source further comprises at least a third X-ray focus point, and the used X-ray detection device further comprises at least third detector elements having a different spectral sensitivity compared to the first and the second detector elements, respectively. The method described with this embodiment further comprises the step of moving the X-ray focus in a discrete manner from the second X-ray focus point to the third X-ray focus point and the step of acquiring third X-ray attenuation data. Thereby, the steps of acquiring the first, the second and the third attenuation data each include a separate data acquisition with the first, with the second and with the third detector elements. Further, the second and the third X-ray focus points are spatially separated from each such that a third beam path originating from the third X-ray focus point penetrates said voxel and impinges on a third detector element.

The method described with this embodiment of the invention has the advantage that triple-energy X-ray attenuation data of the object under examination may be acquired. This may provide even more detailed information of the X-ray attenuation behavior of the object under examination.

At this point it has to be mentioned that the described method may also be expanded to a fourfold-energy or even to a higher multiple-energy CT method.

According to a further aspect of the invention there is provided a computed tomography system for measuring dual-energy X-ray attenuation data of an object under examination. The computed tomography system comprises a rotatable holder being rotatable around a rotation axis and an X-ray source comprising a first X-ray focus point and a second X-ray focus point, the X-ray source being mounted at the rotatable holder. The computed tomography system further comprises an X-ray detection device comprising a plurality of detector elements, the detector elements being divided into a first group of first detector elements and a second group of second detector elements, wherein the first and the second detector elements exhibit different spectral sensitivities, and the X-ray detection device being mounted at the rotatable holder opposite to the X-ray source with respect to the rotation axis.

Furthermore, the computed tomography system comprises a control unit, which is coupled to the X-ray source and to the X-ray detection device and which is adapted for performing the following operation:

(a) Adjusting the X-ray source such that it emits X-rays originating from the first X-ray focus point, (b) acquiring first X-ray attenuation data separately with the first detector elements and with the second detector elements, (c) moving the X-ray focus from the first X-ray focus point to the second X-ray focus point, and (d) acquiring second X-ray attenuation data separately with the first detector elements and with the second detector elements. Thereby, the two X-ray focus points are spatially separated from each such that a first beam path originating from the first X-ray focus point penetrates a certain voxel within the object and impinges on a first detector element and a second beam path originating from the second X-ray focus point penetrates the same voxel and impinges on a second detector element, and wherein the X-ray focus is moved in a discrete manner from the first X-ray focus point to the second X-ray focus point.

According to an embodiment of the present invention, the X-ray focus points are arranged in a plane perpendicular to the rotation axis. This may provide the advantage that the spatial resolution of the acquired X-ray attenuation data can be improved in a simple and effective manner e.g. by a controlled focusing of electrons on the two different X-ray focus points on the anode of the X-ray source.

According to a further embodiment of the invention, the first detector elements and/or the second detector elements exhibit an energy-discrimination. This may provide the advantage that the spectral sensitivity of the detector elements can be realized by appropriate operating conditions of the detector elements. Furthermore, the spectral sensitivity of the detector elements may be varied in order to optimally adapt the spectral ranges of the detector elements to the current measurement conditions.

According to a further embodiment of the invention, the first and the second detector elements are arranged within the X-ray detection device in an alternating manner. Preferably, every second detector element within a row of detector elements is a first detector element or a second detector element.

However, as has already been mentioned above in connection with a triple-energy or a multiple-energy CT method, in case of three different X-ray focus points and three different types of detector elements the periodicity of the detector element within the X-ray detection device may be adapted accordingly.

According to a further embodiment of the invention, the spectral sensitivities of the first detector elements and of the second detector elements, respectively, are realized by means of an X-ray absorption device, which is arranged in front of the X-ray detection device. Such a static post-filtering, wherein the energy separation is carried out after the X-rays have traversed the object under examination can be used to modify cheaply current medical CT scanner e.g. for the use in baggage inspection.

According to a further embodiment of the invention, the X-ray absorption device comprises alternating sections with spectral different X-ray absorption properties. Preferably, the X-ray absorption device may be a comb like structure, which affects the spectral distribution of the radiation being traversed to every second detector element.

A comb-like structure has the advantage that it represents a comparatively cheap element. Therefore, dual-energy scans may be accomplished without a complex and costly modification of known single-energy CT scanners.

It is clear, that when performing triple-energy CT the absorption device is adapted to influence the spectral distribution of the radiation impinging on every third detector element. For multiple-energy CT the absorption device must exhibit an even higher periodicity.

According to a further embodiment of the invention, the X-ray absorption device is detachably mounted in front of the X-ray detection device. This may provide the advantage that the X-ray absorption device can be removed quickly in order to change the setting between dual-energy CT and single-energy CT. Preferably, the X-ray absorption device may be mounted to the X-ray absorption device by means of a hinge or by means of any arbitrary quick coupling device.

According to a further embodiment of the invention, the X-ray detection device is mounted at the rotatable holder with an offset with respect to a central axis lying in a plane perpendicular to the rotation axis. Thereby, the central axis is defined by the center of the X-ray source and the rotation axis. This so-called offset technique provides the advantage that X-ray attenuation data, which are acquired at two different angular positions of the holder, which angular position differ from each other by 180°, are not redundant.

When dual-energy CT is performed by means of two different detector elements arranged in an alternating series, the offset is preferably one half of the distance between the centers of two neighboring detector elements. Thereby, the beam paths traversing the object at an angular position of the holder of X°+180° lie in between the beam paths traversing the object at an angular position of the holder of X°. Therefore, the spatial resolution may be increased.

According to a further aspect of the invention there is provided a data processing device for measuring dual-energy X-ray attenuation data of an object under examination by means of a computed tomography system. Thereby, there is used a CT scanner according to any one of the above-described exemplary embodiments of the computed tomography systems. The data processing device according to this aspect of the invention comprises a memory for storing dual-energy X-ray attenuation data of an object under examination and a data processor. The data processor is adapted for performing an operation comprising the steps of exemplary embodiments of the above-described method.

According to a further aspect of the invention there is provided a computer-readable medium on which there is stored a computer program for measuring dual-energy X-ray attenuation data of an object under examination by means of a computed tomography system. Thereby, there is used a CT scanner according to any one of the above-described exemplary embodiments of the computed tomography systems. The computer program, when being executed by a processor, is adapted for performing an operation comprising steps of exemplary embodiments of the above-described method.

According to a further aspect of the invention there is provided a program element for measuring dual-energy X-ray attenuation data of an object under examination by means of a computed tomography system. Thereby, there is used a CT scanner according to any one of the above-described exemplary embodiments of the computed tomography systems. The program element, when being executed by a processor, is adapted for performing an operation comprising steps of exemplary embodiments of the above-described method.

The program element may be written in any suitable programming language, such as, for example, C++ and may be stored on a computer-readable medium, such as a CD-ROM. Also, the computer program may be available from a network, such as the World Wide Web, from which it may be downloaded into image processing units or processors, or any suitable computer.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered to be disclosed with this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

Figure 1:
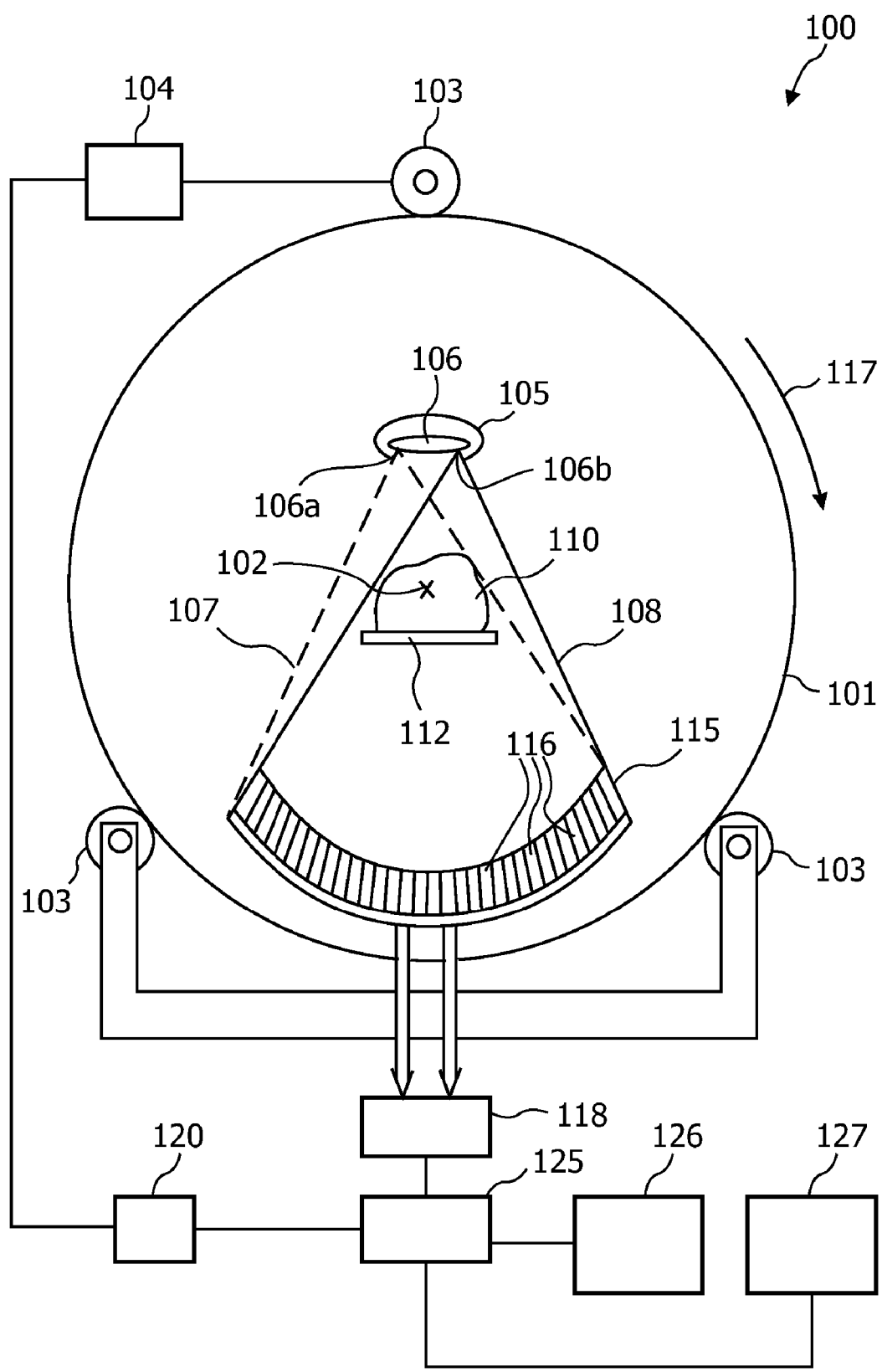
FIG. 1 shows a simplified schematic representation of a dual-energy CT system.

The illustration in the drawing is schematically. It is noted that in different drawings, similar or identical elements are provided with the same reference signs or with reference signs, which are different from the corresponding reference signs only within the first digit and/or with an appended character.

FIG. 1 shows a CT scanner 100 comprising a rotatable holder 101 in which a polychromatic X-ray source 105 and an X-ray detection device 115 are incorporated. The holder 101 is rotated around a rotational axis 102 by means of a drive motor 104 and a drive mechanism. The drive mechanism is symbolized by means of three drive rollers 103. The rotation of the holder 101 may be accomplished in a continuous or in a stepwise manner.

The CT scanner 100 further comprises a table 112, which is arranged such that an object under examination 110 may be positioned in the center of the holder 101. The table 112 may be movable with respect to the gantry 101 in a direction parallel to the rotational axis 102 such that different portions of the object 110 can be examined.

The X-ray detection device 115 contains a row of interconnected detector elements 116, here arranged along an arc of circle. The detector elements 116 can all be read out separately via a preamplifier 118 and a data processing device 125. The data processing device 125 is capable of converting the measured detector signals. By measuring data attenuation signals under a variety of different viewing angles of the system X-ray source 105 with respect to the object 110, the data processing device 125 is capable of reconstructing a three dimensional image of the object 110. The reconstructed images may be outputted by means of a monitor 126 and/or by means of a printer 127.

The data processing device 125 is further coupled with a motor control unit 120, which is used for controlling the movement of the rotatable holder 101 in a rotation direction indicated by an arrow 117.

The X-ray source 105 is an X-ray tube with an elongated anode 106. The anode 106 is elongated in a direction perpendicular to the rotational axis 102. An electron beam emitted by a cathode, which is not indicated here, can be directed discretely onto one of two X-ray focus points, onto a first X-ray focus 106a and onto a second X-ray focus 106b. If the electron beam is directed onto the first X-ray focus 106a, a first radiation beam 107 is emitted from the X-ray source 105. If the electron beam is directed onto the second X-ray focus 106b, a second radiation beam 108 is emitted from the X-ray source 105.

In order to provide for a synchronization between the spatially switching the electron beam between the two focus points 106a and 106b and the data acquisition the data processing device 125 is further coupled with an electronic control unit (not depicted).

The detector elements 116 of the X-ray detection device are divided into a first group of first detector elements and a second group of second detector elements. The first detector elements and the second detector elements exhibit different spectral sensitivities. According to the embodiment described here, this different spectral sensitivity is achieved by means of an X-ray absorption device (not depicted in FIG. 1). This X-ray absorption device, which is mounted in front of the input windows of the detector elements, has a comb like structure with a periodicity such that every second detector element is covered with the X-ray absorption device. The material of the X-ray absorption device is selected such that it modifies the spectral distribution of the X-rays being transmitted through the X-ray absorption device.

Figure 2:
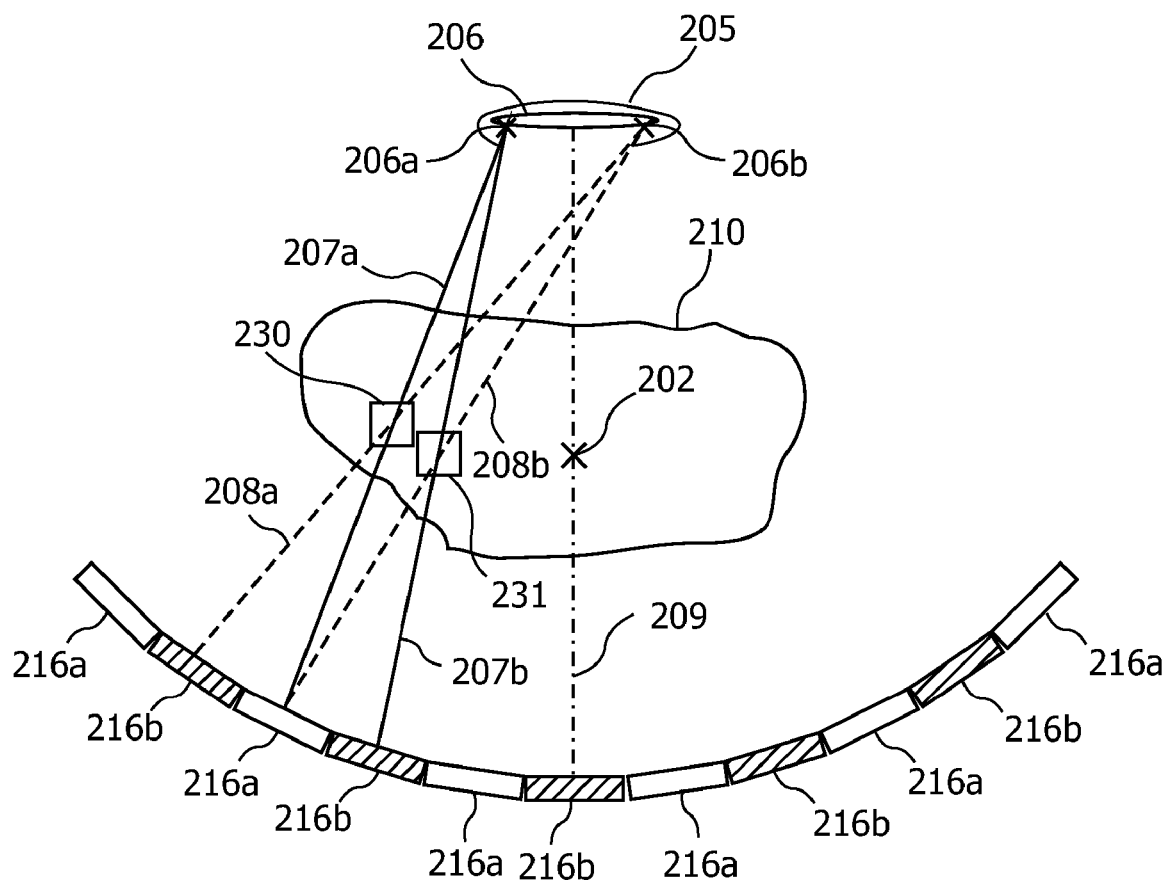
FIG. 2 shows a diagram illustrating dual-energy measurements by means of two different X-ray beams originating from two different X-ray focus points, respectively.

FIG. 2 shows a schematic diagram illustrating dual-energy measurements by means of two different X-ray beams originating from two different X-ray focus points, respectively. An X-ray source 205 having an elongated anode 206 rotates together with an X-ray detection device 215 around a rotation axis 202. FIG. 2 shows the CT system at one angular position. Thereby, the center of the X-ray source 205, the rotation axis 202 and the center of the X-ray detection device 215 are arranged on a virtual central axis 209.

The anode 206 comprises two X-ray focus points, a first X-ray focus 206a and a second X-ray focus 206b. From the first X-ray focus 206a there is originating a first X-ray beam, which is depicted by two first beam paths 207a and 207b, respectively. From the second X-ray focus 206b there is originating a second X-ray beam, which is depicted by two second beam paths 208a and 208b, respectively.

The X-ray detection device 215 comprises first detector elements 216a and second detector elements 216b, which are arranged in an alternating manner, typically along an arc of a circle. However, also planar detector elements may be used. The first detector elements 216a and the second detector elements 216b exhibit a different spectral sensitivity for detecting X-ray photons emitted from the anode 206.

As can be seen from FIG. 2, the first beam path 207a originating from the first focus point 206a penetrates a voxel 230 and impinges on a first detector element 216a. By switching the X-ray focus to the second focus point 206b the voxel 230 is penetrated by the second beam path 208a impinging one a second detector element 216b. Thereby, apart from the X-ray attenuation caused by other voxels the contribution of the X-ray attenuation caused by the voxel 230 can be detected for two different spectral distributions. These distributions are determined by the spectral sensitivities of the first detector element 216a and the second detector element 216b, respectively. The same holds for the attenuation caused by the voxel 231, which is penetrated by the first beam path 207b and by the second beam path 208b, respectively.

By rotating the X-ray source 205 together with the X-ray detection device 215 around a rotation axis 202 it is possible to measure the X-ray attenuation caused by the object 210 at a plurality of viewing angles. Thereby, for each viewing angle there may be acquired two different data sets representing the X-ray attenuation for two different photon energies, respectively. In this respect the term viewing angle is defined by a certain angular position of the X-ray source 205 with respect to the object under examination 210. This means, that each viewing angle comprises two different projection angles depending on the active X-ray focus point.

Initially, each data set representing the X-ray attenuation for a defined spectral distribution comprises a reduced spatial resolution because only every other detector element is assigned to the defined spectral distribution. However, the full spatial resolution may be reached by combining the acquired attenuation data in an appropriate manner. In order to achieve the full spatial resolution it is necessary, that the distances between the centers of the detector elements 216a and the neighboring detector elements 216b correspond to full sampling distance defined by the spacing between the first focus point 206a and the second focus point 206b. This can be seen from FIG. 2 by the matter of fact, that at the depicted viewing angle the voxel 230 is captured with a first spectral distribution by means of the first beam path 207a and with a second spectral distribution by means of the second beam path 208a. The same holds mutatis mutandis for the voxel 231 and all other voxel (not depicted) within the object 210.

Figure 3:
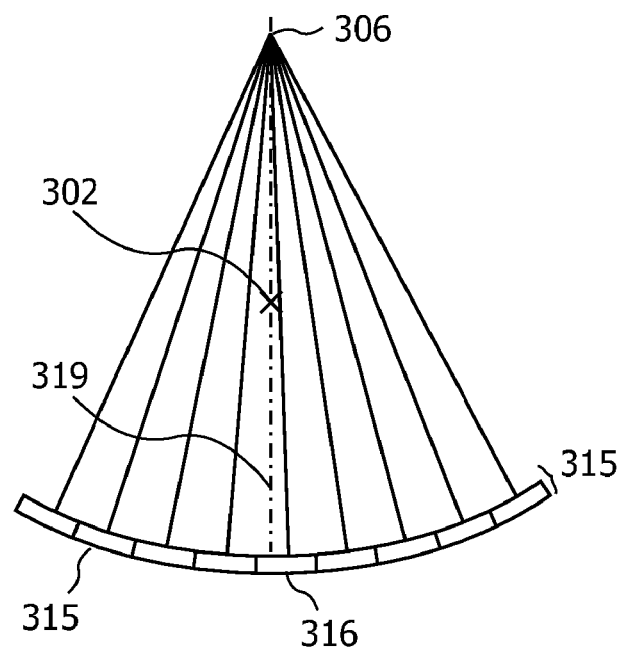
FIG. 3 shows a diagram illustrating the non-redundant data acquisition by employing the so-called offset technique.

FIG. 3 shows a diagram illustrating the non-redundant data acquisition by employing the so-called ray offset technique. For sake of simplicity the ray offset technique is illustrated with an X-ray source comprising one focal spot only. However, the principles of the offset technique may also be applied for the above described dual-energy measurement.

As can be seen from FIG. 3, an X-ray detection device 315 is shifted with respect to a central axis 309 by one quarter of the distance between the centers of two neighboring detector elements 316. This has the effect, that when the angular position of the X-ray focus 306 and the X-ray detection device 315 with respect to the rotation axis 302 is changed by 180°, the spatial course of the beam paths between the X-ray focus 306 and the detector elements 316 interleave. This has the effect, that there is no redundancy of the acquired attenuation data for an angular position X° compared with the corresponding attenuation data measured at an angular position X°+180°.

It has to be noted that in case of the above described dual-energy measurements the periodicity of the detector elements is different by a factor of two, because only every other detector element has the same spectral sensitivity. As a consequence, for applying the offset-technique for the above described dual-energy measurements, an offset of half of the distance between the centers of two neighboring detector elements 316 is optimal in order to realize a symmetric interleaving of the X-ray paths at angular positions differing by 180°, if only one focal spot is used.

If the ray offset technique should be used in combination with two different X-ray beams originating from two different X-ray focus points, an offset of one quarter of the distance between the centers of two neighboring detector elements 316 is optimal.

Figure 4:
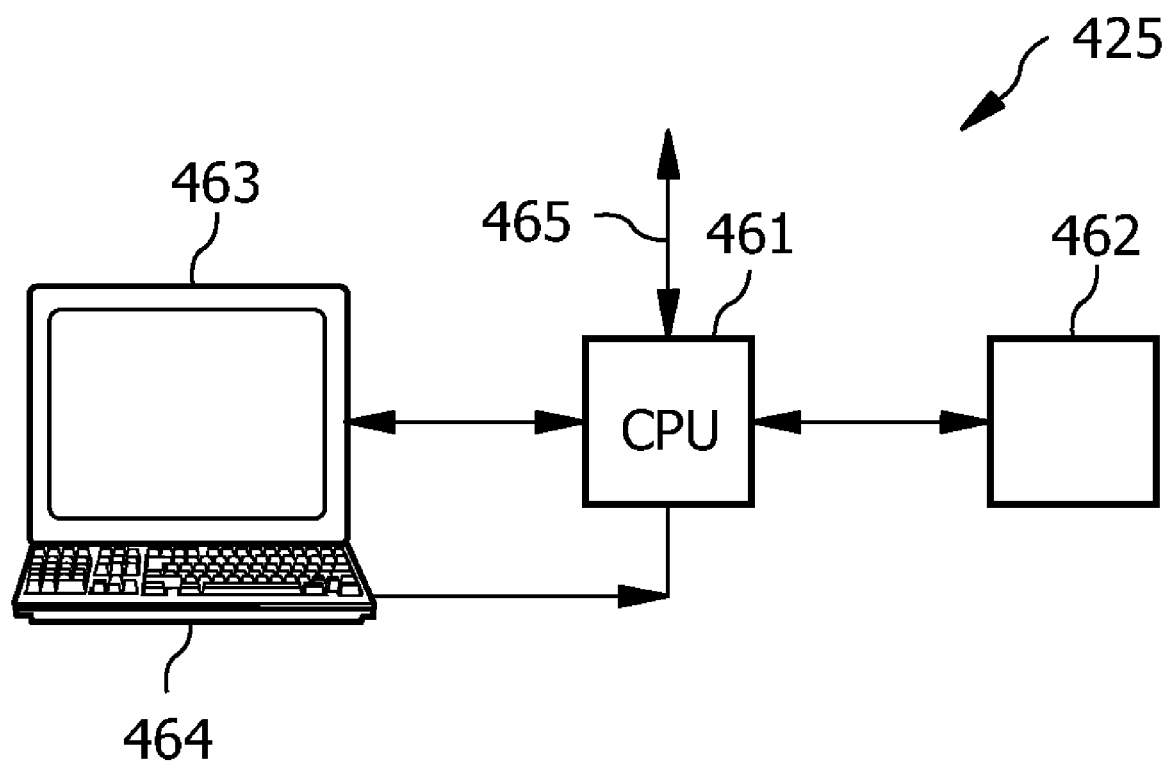
FIG. 4 shows a data processing device for executing an exemplary embodiment of a method in accordance with the present invention.

FIG. 4 depicts an exemplary embodiment of a data processing device 425 according to the present invention for executing an exemplary embodiment of a method in accordance with the present invention. The data processing device 425 comprises a central processing unit (CPU) or image processor 461. The image processor 461 is connected to a memory 462 for temporally storing acquired projection data. Via a bus system 465 the image processor 461 is connected to a plurality of input/output network or diagnosis devices, such as a CT scanner. Furthermore, the image processor 461 is connected to a display device 463, for example a computer monitor, for displaying information or one ore more images reconstructed by the image processor 461. An operator or user may interact with the image processor 461 via a keyboard 564 and/or any other output devices, which are not depicted in FIG. 4.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

LIST OF REFERENCE SIGNS 100 computer tomography apparatus/CT scanner
101 rotatable holder/gantry
102 rotational axis
103 drive rollers
104 drive motor
105 polychromatic X-ray source
106 elongated anode
106a first X-ray focus
106b second X-ray focus
107 first radiation beam
108 second radiation beam
110 object under examination
112 table
115 X-ray detection device
116 detector elements
117 rotation direction
118 preamplifier
120 motor control unit
125 data processing device (incl. reconstruction unit)
126 monitor
127 printer
202 rotational axis
205 polychromatic X-ray source
206 elongated anode
206a first X-ray focus
206b second X-ray focus
207a first beam path impinging onto first detector element
207b first beam path impinging onto second detector element
208a second beam path impinging onto second detector element
208b second beam path impinging onto first detector element
209 central axis
215 X-ray detection device
216a first detector element
216b second detector element
230 voxel
231 voxel 302 rotational axis
306 X-ray focus
309 central axis
315 X-ray detection device
316 detector element
425 data processing device
461 central processing unit/image processor
462 memory
463 display device
464 keyboard
465 bus system

The invention claimed is:

1. A method for measuring dual-energy X-ray attenuation data of an object under examination by means of a computed tomography system, the tomography system comprising
   a rotatable holder being rotatable around a rotation axis,
   an X-ray source comprising a first X-ray focus point and a second X-ray focus point, the X-ray source being mounted at the rotatable holder, and
   an X-ray detection device comprising a plurality of detector elements,
   the detector elements being divided into a first group of first detector elements and a second group of second detector elements, wherein the first and the second detector elements exhibit different spectral sensitivities, and
   the X-ray detection device being mounted at the rotatable holder opposite to the X-ray source with respect to the rotation axis,
   the method comprising the steps of:
   adjusting the X-ray source such that it emits X-rays originating from the first X-ray focus point,
   acquiring first X-ray attenuation data separately with the first detector elements and with the second detector elements,
   moving the X-ray focus from the first X-ray focus point to the second X-ray focus point, and
   acquiring second X-ray attenuation data separately with the first detector elements and with the second detector elements,
   wherein the two X-ray focus points are spatially separated from each other such that a first beam path originating from the first X-ray focus point penetrates a certain voxel within the object and impinges on a first detector element and a second beam path originating from the second X-ray focus point penetrates the same voxel and impinges on a second detector element, and
   wherein the X-ray focus is moved in a discrete manner from the first X-ray focus point to the second X-ray focus point.

2. The method according to claim 1, further comprising the steps of
   combining the first X-ray attenuation data acquired with the first detector elements with the second X-ray attenuation data acquired with the first detector elements, and/or
   combining the first X-ray attenuation data acquired with the second detector elements with the second X-ray attenuation data acquired with the second detector elements.

3. The method according to claim 1, wherein
   the first detector element being impinged by the first beam path and the second detector element being impinged by the second beam path are neighboring detector elements.

4. The method according to claim 1, wherein
   the steps of adjusting the X-ray source, acquiring first X-ray attenuation data, moving the X-ray focus and acquiring second X-ray attenuation data are carried out at a plurality of different viewing angles defined by the angular position of the rotatable holder.

5. The method according to claim 4, wherein
   an attenuation map representing the X-ray attenuation data of a plurality of voxels within the object under examination is generated, and
   the attenuation map is taken into account for a data evaluation of a further radiological examination method.

6. The method according to claim 1, wherein
   dual-energy X-ray attenuation data of a baggage item are measured.

7. The Method according to claim 1, wherein the X-ray source further comprises at least a third X-ray focus point, and the X-ray detection device further comprises at least third detector elements having a different spectral sensitivity compared to the first and the second detector elements, respectively,
   the method further comprising the steps of
   moving the X-ray focus in a discrete manner from the second X-ray focus point to the third X-ray focus point, and
   acquiring third X-ray attenuation data,
   wherein
   the steps of acquiring the first, the second and the third attenuation data each include a separate data acquisition with the first, with the second and with the third detector elements, and
   wherein
   the second and the third X-ray focus points are spatially separated from each such that a third beam path originating from the third X-ray focus point penetrates said voxel and impinges on a third detector element.

8. A computed tomography system for measuring dual-energy X-ray attenuation data of an object under examination, the computed tomography system comprising
   a rotatable holder being rotatable around a rotation axis,
   an X-ray source comprising a first X-ray focus point and a second X-ray focus point, the X-ray source being mounted at the rotatable holder,
   an X-ray detection device comprising a plurality of detector elements,
   the detector elements being divided into a first group of first detector elements and a second group of second detector elements, wherein the first and the second detector elements exhibit different spectral sensitivities, and
   the X-ray detection device being mounted at the rotatable holder opposite to the X-ray source with respect to the rotation axis, and
   a control unit,
   which is coupled to the X-ray source and to the X-ray detection device and which is adapted for performing the following operation:
   adjusting the X-ray source such that it emits X-rays originating from the first X-ray focus point,
   acquiring first X-ray attenuation data separately with the first detector elements and with the second detector elements,
   moving the X-ray focus from the first X-ray focus point to the second X-ray focus point, and
   acquiring second X-ray attenuation data separately with the first detector elements and with the second detector elements, wherein the two X-ray focus points are spatially separated from each other such that a first beam path originating from the first X-ray focus point penetrates a certain voxel within the object and impinges on a first detector element and a second beam path originating from the second X-ray focus point penetrates the same voxel and impinges on a second detector element, and wherein the X-ray focus is moved in a discrete manner from the first X-ray focus point to the second X-ray focus point.

9. The computed tomography system according to claim 8, wherein the X-ray focus points are arranged in a plane perpendicular to the rotation axis.

10. The computed tomography system according to claim 8, wherein the first detector elements and/or the second detector elements exhibit an energy discrimination.

11. The computed tomography system according to claim 8, wherein the first and the second detector elements are arranged within the X-ray detection device in an alternating manner.

12. The computed tomography system according to claim 8, wherein the spectral sensitivities of the first detector elements and of the second detector elements, respectively, are realized by means of an X-ray absorption device, which is arranged in front of the X-ray detection device.

13. The computed tomography system according to claim 12, wherein the X-ray absorption device comprises alternating sections with spectral different X-ray absorption properties.

14. The computed tomography system according to claim 13, wherein the X-ray absorption device is detachably mounted in front of the X-ray detection device.

15. The computed tomography system according to claim 8, wherein the X-ray detection device is mounted at the rotatable holder with an offset with respect to a central axis lying in a plane perpendicular to the rotation axis, wherein the central axis is defined by the center of the X-ray source and the rotation axis.

16. A computer-readable medium on which there is stored a computer program for measuring dual-energy X-ray attenuation data of an object under examination by means of a computed tomography system, the tomography system comprising a rotatable holder being rotatable around a rotation axis, an X-ray source comprising a first X-ray focus point and a second X-ray focus point, the X-ray source being mounted at the rotatable holder, and an X-ray detection device comprising a plurality of detector elements, the detector elements being divided into a first group of first detector elements and a second group of second detector elements, wherein the first and the second detector elements exhibit different spectral sensitivities, and the X-ray detection device being mounted at the rotatable holder opposite to the X-ray source with respect to the rotation axis, which computer program, when being executed by a processor, is adapted for performing the following operation:

adjusting the X-ray source such that it emits X-rays originating from the first X-ray focus point, acquiring first X-ray attenuation data separately with the first detector elements and with the second detector elements, moving the X-ray focus from the first X-ray focus point to the second X-ray focus point, and acquiring second X-ray attenuation data separately with the first detector elements and with the second detector elements, wherein the two X-ray focus points are spatially separated from each other such that a first beam path originating from the first X-ray focus point penetrates a certain voxel within the object and impinges on a first detector element and a second beam path originating from the second X-ray focus point penetrates the same voxel and impinges on a second detector element, and wherein the X-ray focus is moved in a discrete manner from the first X-ray focus point to the second X-ray focus point.

17. A method of generating a tomographic image comprising acquiring first x-ray data from an x-ray source with a first focal point with a first set of detector elements;

acquiring second x-ray data from the x-ray source with a second focal point with a second set of detector elements;

wherein the x-ray source moves between the first focal point and the second focal point in a discrete manner.

18. The method of claim 17 wherein the first set of detector elements and the second set of detector elements exhibit different spectral sensitivities.

* * * * *